United States Patent [19]
Gradon et al.

[11] Patent Number: 5,468,961
[45] Date of Patent: Nov. 21, 1995

[54] INFRARED GAS ANALYSER AND HUMIDITY SENSOR

[75] Inventors: Lewis Gradon; Andrew B. Clark; Paul J. Seakins, all of Auckland, New Zealand

[73] Assignee: Fisher & Paykel Limited, Auckland, New Zealand

[21] Appl. No.: 221,037

[22] Filed: Mar. 31, 1994

Related U.S. Application Data

[63] Continuation-in-part of Ser. No. 957,240, Oct. 6, 1992, abandoned.

[30]      Foreign Application Priority Data

Oct. 8, 1991 [NZ] New Zealand ............................ 240154

[51] Int. Cl.⁶ ................................................. G01N 21/61
[52] U.S. Cl. ............................................................ 250/343
[58] Field of Search ........................... 250/339.03, 339.1, 250/343, 345

[56]                References Cited

U.S. PATENT DOCUMENTS

| | | | |
|---|---|---|---|
| 3,636,768 | 1/1972 | Tinet et al. | 250/349 |
| 4,011,859 | 3/1977 | Frankenberger | 250/343 |
| 4,297,579 | 10/1981 | Spaeth | 250/343 |
| 4,322,621 | 3/1982 | Aargard | 250/343 |
| 4,535,241 | 8/1985 | Eberhardt | 250/343 |
| 4,899,053 | 2/1990 | Lai et al. | 250/343 |
| 5,092,342 | 3/1992 | Hattendorff et al. | 250/345 |

FOREIGN PATENT DOCUMENTS

| | | |
|---|---|---|
| 2582097 | 11/1986 | France . |
| 2316078 | 3/1983 | Germany . |
| 1073644 | 2/1984 | U.S.S.R. . |

Primary Examiner—Carolyn E. Fields
Attorney, Agent, or Firm—Trexler, Bushnell, Giangiorgi & Blackstone, Ltd.

[57]         ABSTRACT

An infrared gas analyser. The analyser comprises a sample cell located in a gas flow, a source of infrared radiation of selected wavelengths which is propagated through the sample cell and an infrared detector which receives radiation which has passed through the cell, The radiation incident on the detector provides a measure of the concentration of selected substances in the gas flow due to one of the wavelengths being selected to be absorbed by the gas being measured. One preferred use is as a humidity sensor in a medical respiratory circuit where at least one selected wavelength is a wavelength strongly absorbed by water. Heating means are associated with the sample cell to vaporize any liquid water which may enter it and the cell is provided with internal baffles to reduce deposition or condensation of water on internal surfaces through which infrared radiation must pass. In one embodiment two selected wavelengths are derived from a single source with the second reference wavelength being a wavelength which is not significantly absorbed by the gas being measured and the source is switched between two power supplies to ensure the output of the detector is equal for the two wavelengths when the concentration of the measured gas is zero.

In a second embodiment two single wavelength sources are used and their combined outputs passed through the sample cell.

7 Claims, 7 Drawing Sheets

INFRARED GAS ANALYSER AND HUMIDITY SENSOR

CROSS REFERENCE TO RELATED SPECIFICATION

This application is a continuation-in-part of application Ser. No. 07/957240 filed Oct. 6, 1992, now abandoned.

BACKGROUND OF THE INVENTION

1. Field of the Invention

The present invention relates to infrared gas analysers particularly though not solely, for use in in-line sensing of the humidity of a humidified gas flow. An application of such an analyser is the sensing of humidity in humidified respiratory gases provided to a patient in a hospital, for example.

2. Description of the Prior Art

Present humidity sensors tend to have rather slow reaction times and are usually not suitable for use in high relative humidities. In the biomedical industry it is often desirable to measure the absolute humidity of a moving airstream which is at a high (60–100%) relative humidity, and with a fast response time.

An example of this application is the measurement of humidity in the breathing circuit of a patient on a ventilator. In this case it is desirable to know the humidity on a breath-by-breath basis or integral over a period of time, in a fast moving air flow, and without being affected by water condensation. The air stream in this system is warmer than the surrounding tube walls so there may be water droplets on the walls of the tube and in the air. It is also desirable to measure the humidity in the breathing circuit without the use of a sampling device (e.g. a suction pump or bypass tube). A device of this type is referred to as "mainstream" and has the advantages of speed, simplicity and quiet operation. Also, the humidity sensor must not affect the humidity being measured to any large extent.

The existing commercial devices for measuring humidity operate on several well known principles, which all have advantages and disadvantages.

Psychrometers are devices which measure the difference in temperature between a wet bulb and a dry bulb thermometer. They axe normally used for meteorology or in rooms or chambers where the humid air is static or slow moving and there is little chance of contamination.

There are many devices, made from polymer films or porous ceramics, which allow the water from humid air to adsorb onto their surface. This results in a change in the device's physical characteristics (e.g. resistance or capacitance), which can be measured. These devices are inexpensive and are popular for HVAC applications and consumer goods. The disadvantages of these devices are that their accuracy is low, long term drift and contamination of the adsorptive surface can occur, and they tend to get "waterlogged" at high relative humidities. This limits their application in a medical breathing circuit, where the relative humidity is often high.

Devices which measure the dew-point of humid air using a chilled mirror are expensive, but are well suited to high relative humidities and are accurate. Disadvantages of the technology are that the surface of the mirror is prone to contamination, and the device works best in still air.

There are commercial devices which measure the heat conductivity of humid air using heated temperature sensors. They are sensitive to the absolute humidity of the air and cope well with high humidifies. However, the measurement can be: affected by the air flow and by differing gas constituents. In a breathing circuit there may be high levels of oxygen or anaesthetic gases which would affect the humidity measurement.

One method of humidity measurement which gives a fast response time and could be made insensitive to variations in air speed and gas composition is infrared humidity sensing.

SUMMARY OF THE INVENTION

It is one object of the present invent/on to provide apparatus for sensing the humidity of a humidified gas or mixture of gases which will go some way towards overcoming the foregoing disadvantages.

It is a further object of the present invention to provide an improved infrared gas analyser.

In one aspect the invention consists in apparatus for measuring the humidity of a gas or a mixture of gases flowing in a medical breathing circuit, said apparatus comprising a source of infrared radiation of one or more selected wavelengths including a wavelength strongly absorbed by water, a gas sample cell through which the radiation is passed and through which said gas or gases pass in use, as infrared radiation detector adapted to detect radiation in said selected wavelengths, means defining a radiation path between said source and said detector with said sample cell being positioned intermediately of said source and said detector, signal processing means connected to the output of said detector which convert the intensity of the received infrared radiation on said detector to a signal proportional to the humidity of the gases passing through said sample cell and means associated with said sample cell which prevent water entering or forming in the sample cell.

In a second aspect the invention consists in an infrared gas analyser comprising a source of infrared radiation of one or more selected wavelengths including wavelengths strongly absorbed by selected gases, a gas sample cell through which the radiation is passed and through which said gas or gases pass in use, an infrared radiation detector adapted to detect radiation in said selected wavelengths, means defining a radiation path between said source and said detector with said sample cell being positioned intermediately of said source and said detector, signal processing means connected to the output of said detector which convert the intensity of the received infrared radiation on said detector to a signal proportional to the concentration of one or more selected substances present in the gases passing through said sample cell and means associated with said sample cell which prevent water entering or forming in the sample cell.

In a third aspect the invention consists in an infrared gas analyser comprising a source of infrared radiation of one or more selected wavelengths including wavelengths strongly absorbed by selected gases, a removable gas sample cell through which the radiation is passed and through which said gas or gases pass in use, an infrared radiation detector adapted to detect radiation in said selected wavelengths, means defining a radiation path between said source and said detector with said sample cell being positioned intermediately of said source and said detector, electrical heating means configured so as to enclose a substantial part of the exterior surface of said sample cell when said sample cell is engaged in said analyser so as to vaporize any liquid water carried in said gas or gases, and heater control means which control the power supplied to said heater means such that the temperature of the gas or gases leaving the chamber is substantially the same as the temperature of the gas or gases entering the chamber.

In a fourth aspect the invention consists in a removable sample cell for an infrared gas analyser comprising a chamber having a gas inlet port and a gas outlet port, at least one infrared transparent window in said chamber which in use aligns with a beam of infrared radiation produced by said analyser, and controlled power electrical heating means disposed about the outer surface of said chamber to heat the chamber so as to vaporize any liquid water carried in said gas, the power supplied to said heating means controllable such that the temperature of the gas leaving the chamber is substantially the same as the temperature of the gas entering said chamber.

DETAILED DESCRIPTION OF THE PREFERRED EMBODIMENT

If radiation in the near and medium infrared (IR) spectrum is passed through a material it is possible to see bands of absorption which indicate the chemical composition of the material. In air there are five major components, i.e. nitrogen, oxygen, argon, carbon dioxide and water vapor. Of these components nitrogen, oxygen and argon do not absorb infrared radiation because they have a symmetrical structure. Carbon dioxide has a strong absorption band at 4.3 μ/wavelength and water vapor has absorption bands at 1.35–1.45 μm, 2.6–2.8 μm and at 5.5–6.5 μm wavelength. In a medical environment there may be other gases (e.g. anaesthetics) present in the air which will introduce absorption bands at other wavelengths.

A device which uses infrared absorption to measure humidity could be constructed as follows. An infrared source (which may be of narrow bandwidth or has a narrow bandwidth filter) is set up so its radiation is collimated into a beam, the beam passes through a chamber (sample cell) contain/rig the sample air, and finally strikes an infrared detector which measures the radiation intensity. The infrared filter is chosen so that it only allows radiation in one of the water absorption bands to pass through. The device may be heated with a heating coil to stop condensation in the measurement cell, or the power of the infrared radiation may be enough to stop condensation. Some modulation of the light source will be necessary to reduce the system noise and increase the long term ability. This may be accomplished either by directly modulating the light source or by using some form of mechanical radiation chopper.

In a practical situation there may be a similar setup with a chamber containing dry air, to be used as a reference (reference cell). The difference in the amount of radiation falling on the sample detector and the reference detector is the amount of radiation which has been absorbed by water vapor. The difference may be related to the amount of water vapor in the sample cell and hence the absolute humidity. This type of system is known as a dual beam, single wavelength system and is well known in the prior art. The advantage of the dual beam, single wavelength system is that if any contaminants build up on the windows of the sample cell then the measurement accuracy is degraded.

An alternative to the dual beam method is to use one sample cell but pass two different wavelengths through it One of the wavelengths is located inside the water absorption band (measurement wavelength) and the other is located outside of a water absorption band (reference wavelength). The two wavelengths are usually created by directly modulating two sources, wavelength modulating a single source, alternating several bandpass interference filters in the radiation path, or wavelength modulating a bandpass interference filter. The amount of radiation that is incident on the infrared detector will depend on the amount of water vapor in the sample cell while the measurement wavelength is being passed through the cell, and independent of the amount of water vapor while the reference wavelength is passed through. Thus a small alternating signal will be present at the output of the detector which, for a constant amount of source radiation, will be proportional to the amount of radiation absorbed by water vapor in the sample cell. This can be related to the amount of water in the sample cell, and hence the absolute humidity.

This type of system is called a single beam, dual wavelength system and is well known in the prior art. The advantage of this type of system is that any doradation of the window surfaces in the sample cell will affect both the measurement and reference wavelengths equally (assuming the wavelengths are close together) and hence will not affect the accuracy of the absolute humidity measurement.

Figure 1:
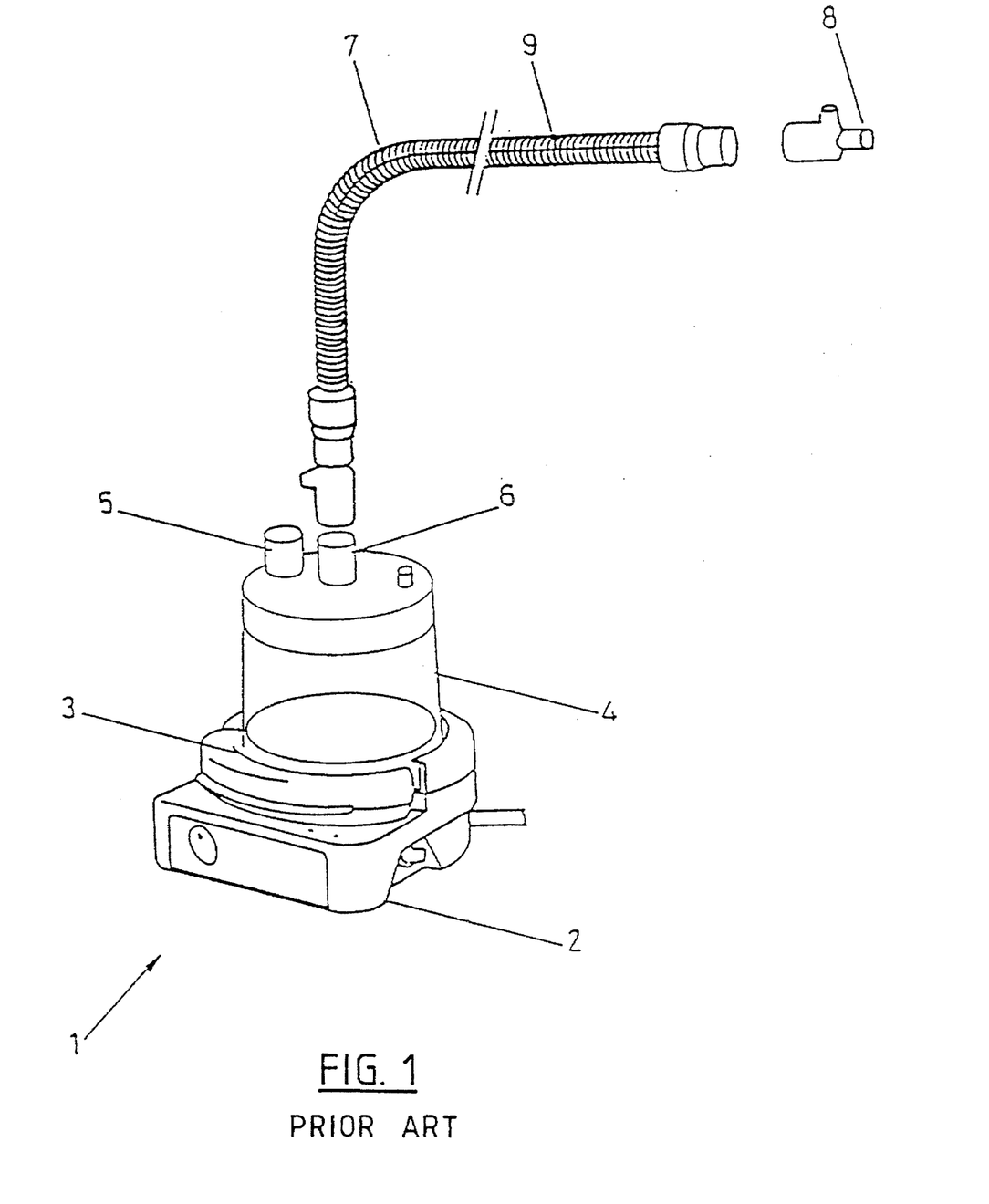
FIG. 1 is a pictorial view of humidifier apparatus.

Apparatus used for humidifying air supply to a patent is well known and is often provided in a form similar to that shown in FIG. 1. Referring to FIG. 1, humidifier apparatus is shown generally referenced 1 comprising a base 2 which includes electronic control circuitry and has a heating element within a heater plate 3, the heater plate being in contact with the base of a humidifying chamber 4. The humidifying chamber has a gases inlet 5 and a gases outlet 6. The gases outlet 6 is provided for connection to a conduit 7 which provides humidified gases to a source at end 8 of the conduit. The source may be connected to a face mask or an intubated patient, for example. A heating element 9 is also provided within the conduit to help prevent the humidified gases condensing as they travel through the conduit. Water is present in the humidifying chamber 4, this water is heated by the heater plate 3 to humidify gases in the humidifying chamber to a desired temperature and desired humidity. Usually condensation will develop in the conduit connecting a user such as a hospitalized patient to the medical breathing circuit which includes a ventilating system and humidifier apparatus for providing the source of the humidified gases. Condensation will develop in the conduit because the walls of the conduit are usually at a lower temperature (a temperature close to the ambient temperature of the surrounding atmosphere) compared with the temperature of the humidified gases supplied by the apparatus. Hitherto, humidity sensors have not been provided which are not affected by water condensation in such a conduit and at the same the provide sufficiently fast, accurate measurement of the humidity of such a fast moving airflow.

Figure 2:
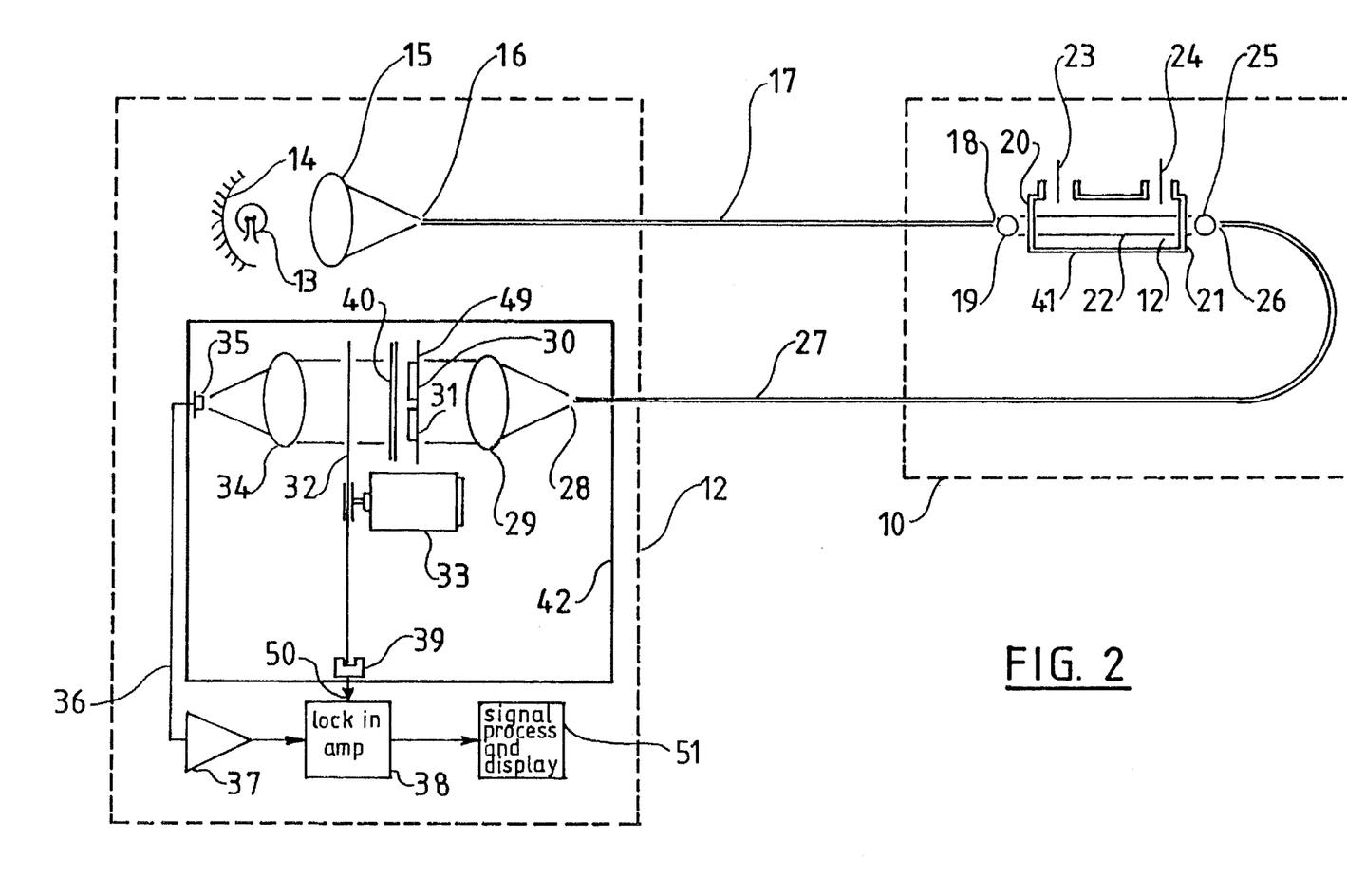
FIG. 2 is a pictorial block diagram of humidity measurement apparatus in accordance with one embodiment of the present invention.

In FIG. 2 a single beam, dual wavelength infrared humidity sensor in accordance with a first embodiment of the invention is shown. It consists of two assemblies, a sensor unit 10 and a remote base unit 12. The base unit 12 is preferably located in or adjacent to the humidifier base 2 (FIG. 1 ) and the sensor unit 10 is located in or comprises part of the breathing conduit 7. Broadband radiation is produced by a tungsten halogen lamp 13 and collimated into a beam by spherical mirrors 14, which may be pan of the halogen lamp assembly. The collimated beam of light is focused by a lens 15 to an image 16 at the end of an optical fibre 17. A portion of the radiation enters the optical fibre and is propagated in the fibre core to the sample cell end of the fibre 18 where it emerges and is collimated by the glass microsphere 19. The beam of parallel radiation passes through the sample cell 41 via windows 20 and 21. The gas which is being measured in the internal space 22 of the sample cell is allowed to move through the sample cell via ports 23 and 24. After emerging from the sample cell the beam of radiation is focused by a second glass microsphere 25 to a point 26 at the end of a second optical fibre 27. The radiation then propagates through the fibre core to the other end of the optical fibre 28 where it emerges from the fibre and is collimated by lens 29 to a parallel beam. This beam then passes through two infrared bandpass filters 30 and 31 which are mounted in an optical baffle 49 so that radiation can only pass through the filters 30 and 31. Filter 30 is a filter which has been chosen to pass only wavelengths which lie in a water absorption band (1.37 µm for example) and is the measurement filter. Filter 31 is a filter which has been chosen to pass only wavelengths which lie outside a water absorption band (1.30 µm for example) and is the reference filter. An optical chopping disk 32 is rotated by a motor 33 and alternately allows radiation from filter 30 and filter 31 to pass through to lens 34 where the radiation is brought to a focus at infrared detector 35, which may be of the germanlure photodiode type. The signal from the detector 35 is electrically connected to amplifier 37 by cable 36 and synchronously detected by lock-in amplifier 38. Means such as a photodiode is provided via photointerrupter 39 for a synchronizing signal 50 to be provided to lock-in amplifier 38. The output of the lock-in amplifier is processed by signal processing and display circuitry 51 which may be analog or digital, to give a measure of the absolute humidity. A housing 42 may be provided around the detector assembly to provide optical isolation. Means is provided (for example by a sliding baffle 40) to vary the amount of radiation coming through filters 30 and 31 so that the detector 35 will give no AC signal when dry air is passed through the sample chamber. This adjustment may be necessary if the filters do not have equal bandwidths or transmittance or if the detector response is not uniform with wavelength.

As an alternative to the tungsten halogen lamp 13 a semiconductor source (for example a light emitting diode ) could be used. As another alternative the spherical mirror 14 and lens 15 could be replaced by an elliptical mirror which would focus the light from the lamp directly to an image 16. As another alternative, the infrared radiation source may be part of the sensing unit 10.

Figure 3:
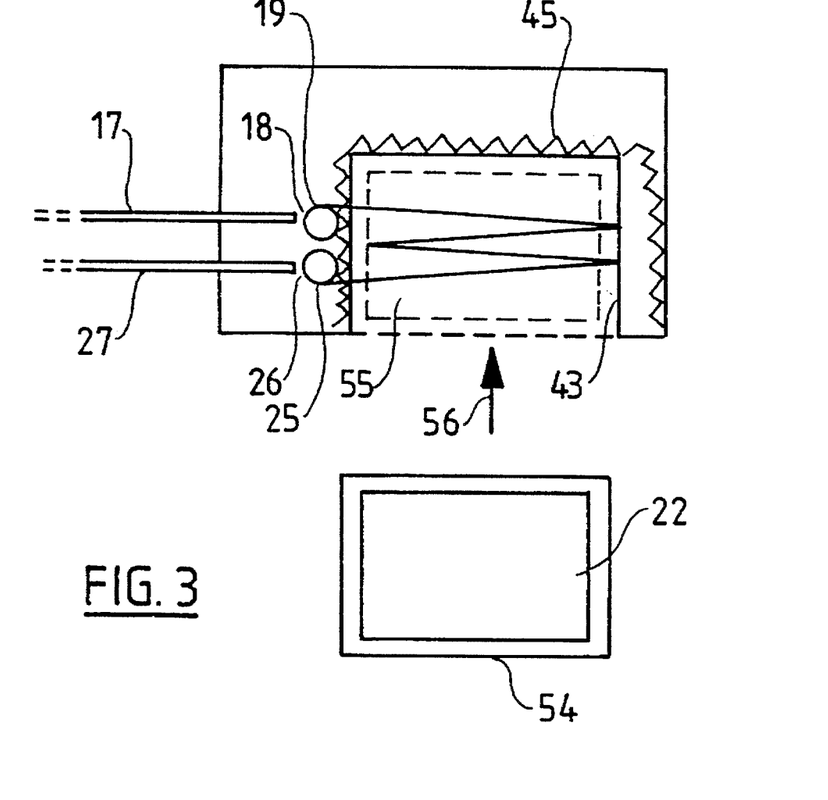
FIGS. 3 and 4 are diagrammatic cross sections of alternative sample cell configurations.
Figure 4:
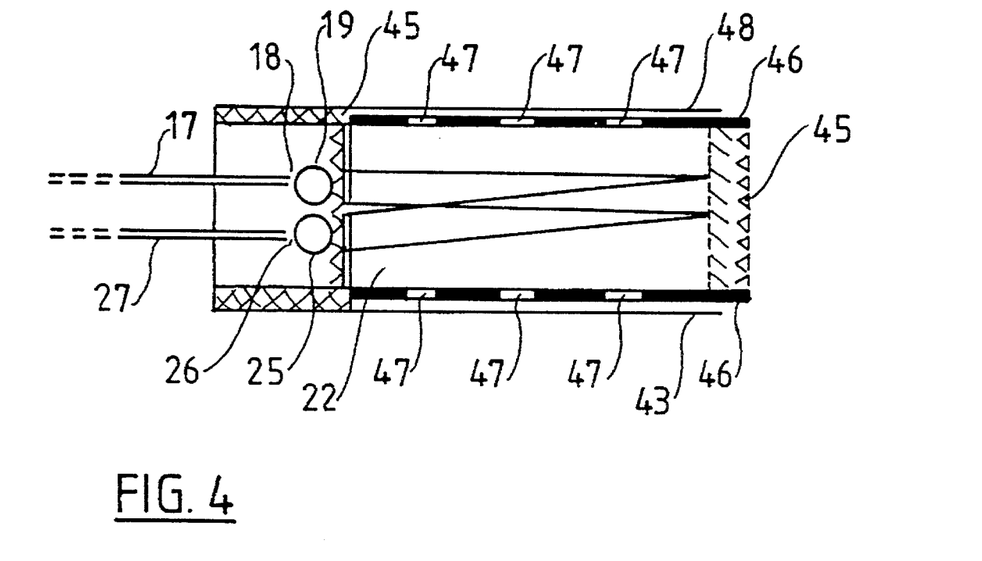

FIGS. 3 and 4 show two sensing unit alternatives. Referring to FIG. 3 instead of the radiation passing directly through the sample cell as shown in FIG. 2 another way of arranging the system would be for a mirror 43 to be placed on one side of the sample cell so that the ends of both optical fibres 18 and 26 can be located next to each other. This means that the optical fibres 17 and 27 can both exit from the sample cell on the same side and can be combined into a single cable. The sample cell 41 and windows 20 and 21 may be combined into a disposable item and may be moulded from plastic in the form of a rectangular tube 54 which is provided in the breathing conduit. The rectangular tube 54 fits into opening 55 in response to a sliding movement by a user in a reflection indicated by arrow 56. The glass microspheres may alternatively be two small lenses or may be raoultied into a plastic sample cell. A heating means, for example a heating cod 45 may be provided to keep the rectangular tube 54 free of condensation which would occur if the dew point of the air was above the temperature of the tube.

Referring to FIG. 4 a further alternative sensing unit would be a probe that could be inserted into a breathing circuit by, for example, inserting it in an appropriate aperture provided in the breathing conduit 7 (FIG. 1). A mirror 43 is again provided so that the optical fibres 7 and 17 can both exit the sample cell from the same side. A plastic support structure 46 is provided to support the mirror 43. The structure 46 has holes 47 to allow the air to be measured to pass through the radiation path. A heater, for example heating cot 45, is provided to keep the sensing unit free of condensation. A hydrophobic, porous envelope 48 of wire mesh or polytetrafluoroethylene (PTFE) may be needed to keep condensation and liquid water away from the radiation path.

The signal from detector 35 will remain proportional to the amount of infrared radiation absorbed by the water vapor in the sample cell as long as the amount of radiation from the lamp 13 remains relatively constant. The most likely cause of this changing would be a long term reduction in signal caused by degradation of the optical components and surfaces and/or ageing of the lamp. One way to reduce this effect would be to measure the amount of light reaching a photodiode mounted for example in front of the optical baffle 39 and either compensate for changes in this overall brightness or control the lamp brightness to keep the signal at this point constant. This would also show if the radiation path was broken (for example by a disconnected optical fibre or obscured sample cell).

A second embodiment of the invention will now be described.

Figure 5:
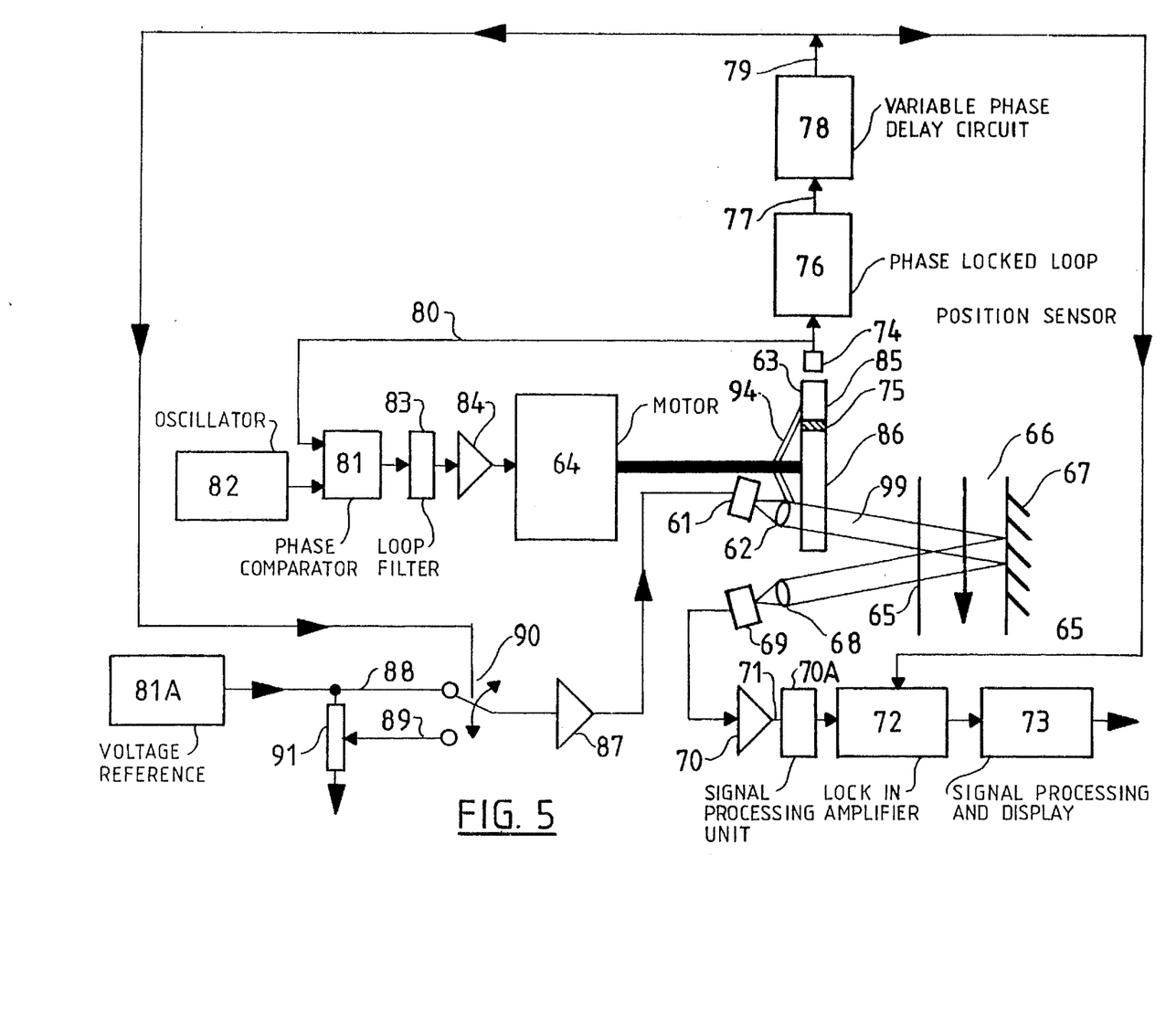
FIG. 5 is a block diagram of an infrared gas analyser according to a second embodiment of the invention.

FIG. 5 shows diagrammatically an alternative single beam, dual wavelength infrared humidity sensor which includes a sample cell as an integral unit. Radiation from an infrared radiation source 61, is collimated by lens 62 into a beam 99. This beam is passed through rotating dual filter assembly 63 which is driven by motor 64. The rotating filter assembly contains two narrow band interference filters 85, 86 which allow first one wavelength then another to pass through the filter assembly as it rotates. Filter 85 allows radiation which is in a water absorption band to pass. Filter 86 avoids the water absorption bands and constitutes a reference filter 86.

The beam then passes through sample cell 65, through which the gases 66 to be analyzed are flowing and is then reflected back off mirror 67 to pass through sample cell 65 a second time. The beam is focused by lens 68 to a point on an infrared detector 69 which may be of the germanium photodiode type. It should be noted that the beam may be reflected a number of times through the sample cell 65 to increase the absorption of radiation by water vapor, or it may not be reflected at all, but passed through the sample cell 65 only once.

The signal from detector 69 is amplified by proamplifier 70 to give an output signal 71, which is synchronously detected by lock-in amplifier 72. The output of the lock-in amplifier is processed by signal processing and display circuitry 73 to give a measure of the absolute humidity.

A position sensor 74 which may be of the reflective optosensor type is used to detect a mark 75 which is present on rotating filter assembly 63. The output signal 80 from this sensor is connected to phase locked loop 76 and this provides a signal 77 which is in phase with the signal from the position sensor 74 and has a 50% duty cycle. A variable phase delay circuit 78 gives a synchronizing signal 79 which is identical to signal 77 but is shifted by a fixed phase angle. The phase delay is adjusted so that synchronizing signal 79 coincides exactly with the timing of the light beam changing from one half of the dual filter assembly to the other. Signal 79 is used for synchronizing the lock-in amplifier 72.

The speed of the motor 64 may be controlled by using phase comparator 81 to compare the phase of signal 80 with a reference frequency signal from oscillator 82. The output of phase comparator 81 passes through loop filter 83 to amplifier 84 which powers the motor. This arrangement forms a phase locked loop which controls the motor speed so that it equals the frequency of oscillator 82.

The infrared radiation source 61 may be an incandescent lamp or preferably a semiconductor light source such as an infrared light emitting diode (LED). The use of an LED as a radiation source allows fast modulation of its light output by varying the amount of current applied to it. The wavelength range of the infrared source 61 must be selected so that it encompasses the reference and measurement wavelengths.

When dry air is passed through the sample cell the output signal 71 of the detector preamplifier will generally be alternating between two levels, being the signal at the measurement wavelength and the signal at the reference wavelength. These are generally not equal due to differences in transmission of the interference filters 85 and 86, differences in the output of the infrared source 61 with wavelength, differences in the wavelength response of the infrared detector 69 and other factors. To "balance" the system, or make the measurement and reference signal levels equal in output signal 71, the amount of current applied to the infrared source 61 can be switched between two levels in time with the rotating of the filter wheel. This may be accomplished by driving the infrared source 61 from a voltage to current converter 87 which has its input switched by analog switch 90 between two voltages 88 and 89, which are derived from voltage reference 81A. The switch 90 is controlled by synchsonising signal 79 so that the current to the infrared source 61 is switched between two levels in time with the rotation of the filter wheel assembly 63. The two voltages 88 and 89 are adjusted using voltage divider 91 so that the output signal 71 has two equal signal levels corresponding to the measurement and reference wavelengths. The system is then considered "balanced" with dry air and there will be a signal of zero at the output of lock-in amplifier 72. Any humidity which is then introduced into the sample cell will attenuate the signal at the measurement wavelength more than at the reference wavelength, and this will cause the output signal 71 to alternate between two different signal levels, and the output of the lock-in amplifier 72 will be non-zero and proportional to absolute humidity.

Figure 6:
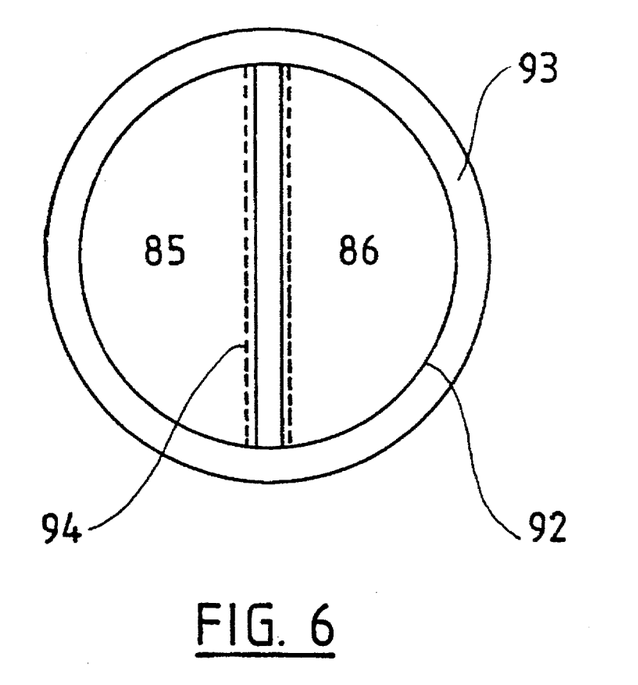
FIG. 6 is a plan view of a rotating filter for the analyser shown in FIG. 5.

FIG. 6 shows a front view of rotating filter 63, made in one possible configuration. The two interference filter halves 85 and 86 are each shaped as a semicircle and combined into a complete filter 92. The filter 92 fits into a filter holder 93 which also includes rib 94. Rib 94 is connected to the shaft of motor 64 and supports the filter assembly during rotation. Rib 94 also covers the join between filter halves 85 and 86 so that infrared radiation cannot leak through.

Figure 7:
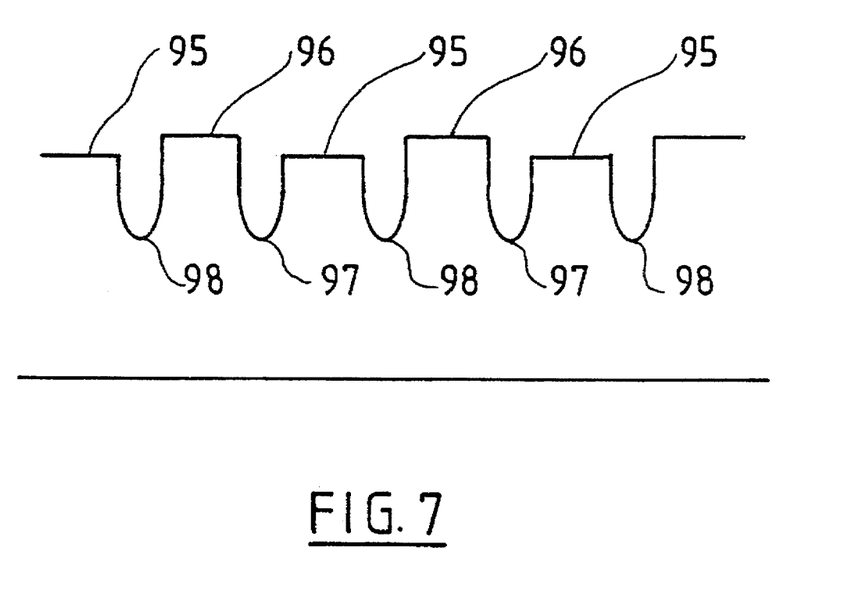
FIG. 7 is a waveform diagram of the output of a radiation detector in the analyser shown in FIG. 5.

FIG. 7 shows a typical output signal 71. There are two signal levels 95, 96 corresponding to the measurement and reference wavelengths. These occur when the radiation beam 99 is passing through the filter halves 85 and 86 respectively. The regions marked 97 and 98 correspond to the times when the radiation beam 99 is being partially or fully blocked by the rib 94 of the filter assembly 63. At these times the signal 71 is somewhat undefined so it may be advantageous to ignore these parts of the signal either by interrupting the signal 71 with a zero level while the radiation beam is being cut by rib 94 or by holding level 95 during interval 97 and holding level 96 during interval 98 signal processing unit 70A to implement these techniques can be included between proamplifier 70 and lock-in amplifier 72. In this way the output signal 71 is defined at all times.

Some of the optical components may be sensitive to temperature so the optical setup may be temperature controlled in accordance with usual practice.

Figure 8:
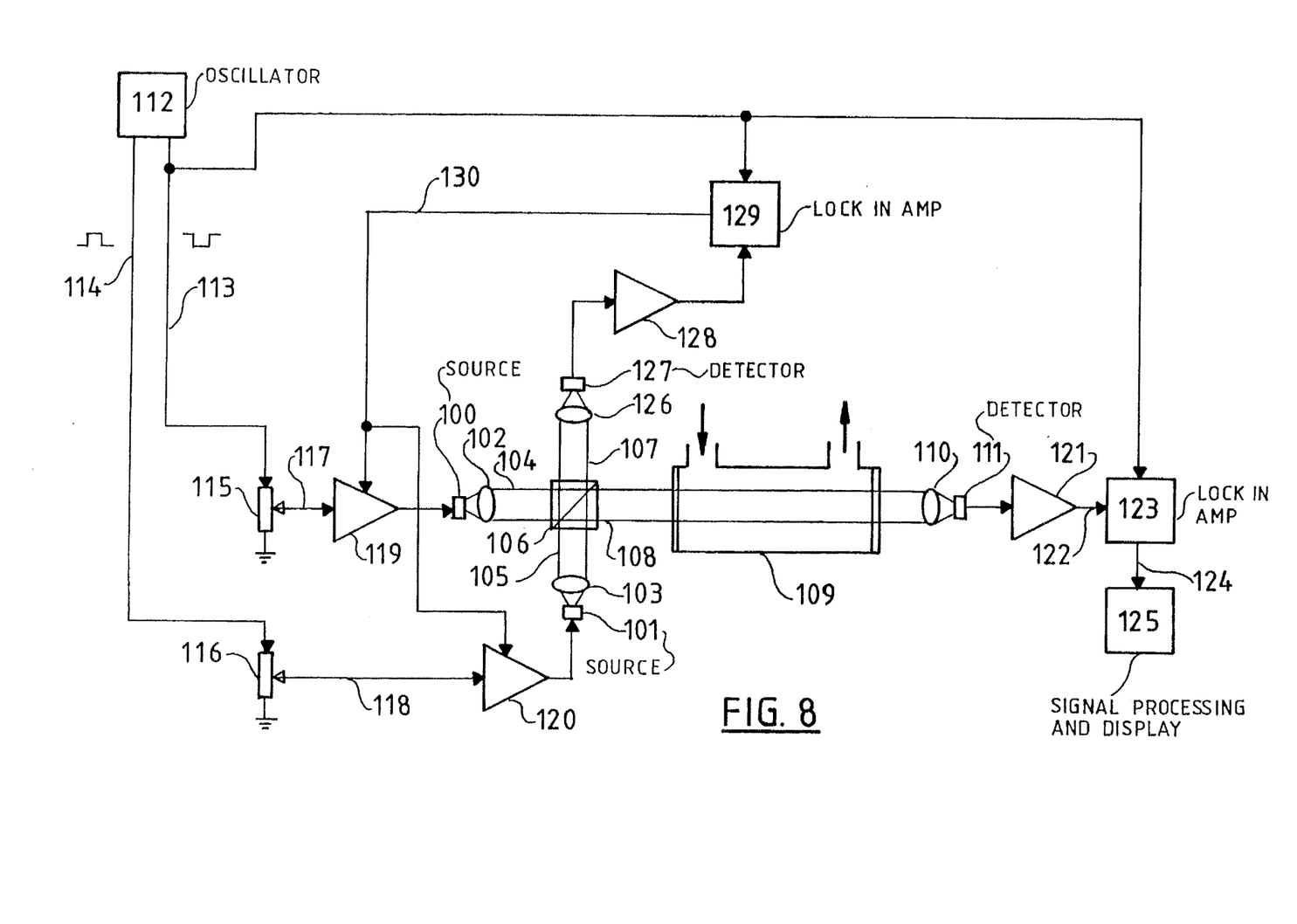
FIG. 8 is a block diagram of an infrared gas analyser according to a third embodiment of the invention.

A third embodiment of the invention will now be described with reference to FIG. 8. Again the sample cell is an integral unit. Two infrared radiation sources 100, 101 are arranged at a right angle and the radiation from each is collimated by lenses 102, 103 into two perpendicular beams 104, 105. The radiation sources 100, 101 may be of the narrow band type, or they may be wide band sources used in conjunction with narrow band filters. The first radiation source 100 has its wavelength chosen to coincide with a water absorption band and this defines the measurement wavelength. The other radiation source 101 has its wavelength chosen to avoid any water absorption bands and this defines the reference wavelength.

The two infrared sources 100, 101 are alternately switched on and off by switching the current supplied to them. Oscillator 112 supplies two switching signals 113, 114 which are square waves, signal 114 being 180° out of phase with signal 113. The voltage level of each square wave is reduced using adjustable voltage dividers 115, 116 to give two square wave signals 117, 118 of differing amplitude. The signals 117, 118 are fed to voltage to current converters 119, 120 which drive the two infrared radiation sources 100, 101.

The beams 104 and 105 are arranged to intersect at a beam splitter 106 which has a transmission/reflection ratio of approximately 1:1 and causes each of beams 104 and 105 to be split almost equally into each of beams 107 and 108. One of the two infrared beams 108 passes through sample cell 109 which contains the water vapor containing gas to be measured and is collimated by lens 110 to a point on infrared detector 111. The radiation beam 108 may be reflected a number of times through the sample cell 109 to increase the absorption of radiation by the water vapor. The signal from detector 111 is amplified by proamplifier 121 to give a detector signal 122. Lock-in amplifier 123 synchronously detects detector signal 122 to give an output signal 124 which is proportional to absolute humidity. The synchronizing signal is supplied to lock-in amplifier 123 by oscillator 112. The output signal 124 is processed by signal processing and display circuitry 125 to give a measure of the absolute humidity, The infared sources 100, 101 in this embodiment produce two different radiation beams 104, 105 which are of two different wavelengths and are switched alternately on and off. The power of each radiation beam 104, 105 is determined by its respective adjustable voltage divider 115 or 116. The voltage dividers 115, 116 are adjusted so that the two automating levels in signal 122 are equal when there is no water vapor in sample cell 109. The system is then considered to be "balanced" and the output 124 of lock-in amplifier 123 will be zero. Any water vapor which is then introduced into sample cell 109 will cause the two alternating levels in signal 122 to be different and the output 124 of lock-in amplifier 123 will be proportional to absolute humidity.

In a variation of this embodiment, a lens 126 may be used to focus the radiation beam 107 down to a point on a second detector 127. The signal from detector 127 is amplified by proamplifier 128 and synchronously detected by lock-in amplifier 129 to give a signal 130 which is a measure of the imbalance of the two wavelengths before entering the sample cell. This signal 130 could be used in a control loop to keep the ratio of the two radiation beams 104, 105 constant over time, by controlling the amount of current being supplied to each infrared source 100, 101. In this way the calibration of the infrared humidity sensor would be prolonged because any variations in the radiation output of the infrared sources 100, 101 would change the balance signal 130 and this would adjust the current being applied to the infrared sources 100, 101 so that their radiation output was the same as before.

Figure 9:
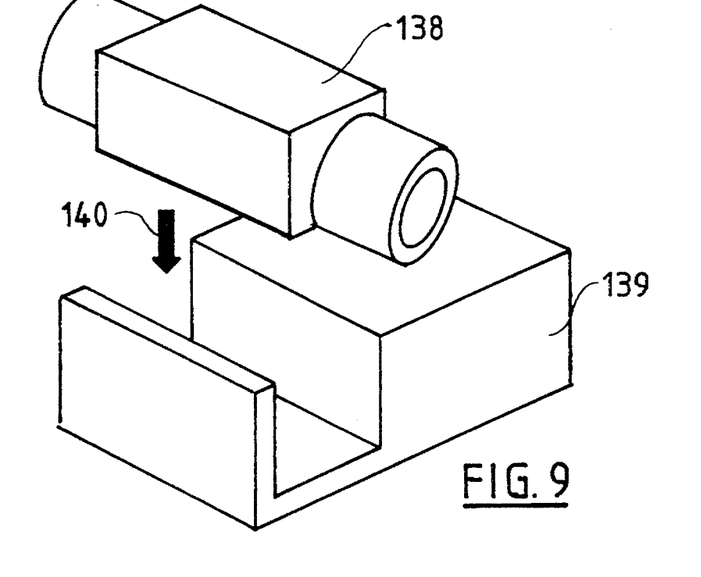
FIG. 9 is a pictorial view of an analyser unit and a removable sample cell.
Figure 10:
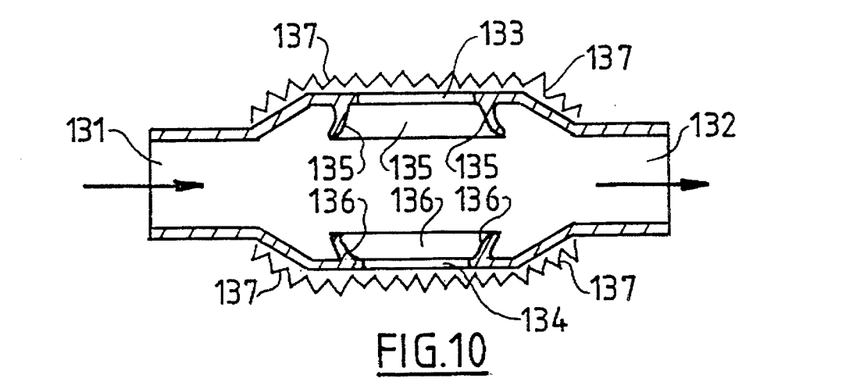
FIG. 10 is a longitudinal sectional view of one form of sample cell.
Figure 11:
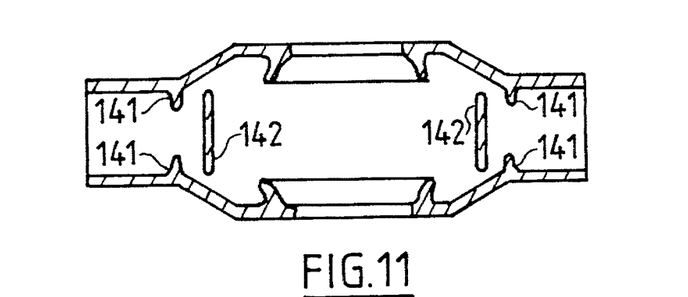
FIG. 11 is a longitudinal sectional view of a second form of sample cell.

A suitable sample cell for the second and third embodiments desert bed above is shown in FIGS. 9 to 11.

FIG. 9 shows in pictorial view a disposable sample cell 138 which is able to be fitted into an infrared humidity sensor unit 139 in response to a sliding movement by the user in the direction shown by arrow 140. The advantage of a disposable sample cell is that it can be removed when it gets contaminated and can be replaced by a new clean, sterile sample cell without having to spend time cleaning the old sample cell. This is particularly important in a medical application.

When using an infrared humidity sensor in a medical breathing circuit, care must be taken to prevent liquid water, which may be present in the breathing circuit from obstructing the optical path or settling on the windows of the sample cell. This may be avoided by heating the sample cell to prevent condensation, by using water baffles or water bypass tubes around the sample cell windows, and by using a microporous membrane around the light path which allows air and humidity to pass through it but not let liquid water through.

FIG. 10 shows a sample cell formed as a tube with a rectangular center portion and with tubular ports 131, 132 at each end. These ports are made with standard medical breathing circuit connectors, so that the sample cell can be connected to medical breathing circuits. Gases to be measured are able to pass in and out of the sample cell through ports 131 and 132. Infrared radiation is able to pass through the sample cell through windows 133 and 134. Baffles 135 and 136 extend all of the way around windows 133 and 134 and these baffles provide some protection against liquid water flowing through ports 131, 132 and onto windows 133, 134. Instead such water is forced to pass around the windows and out through the parts 131, 132. Instead of water baffles, some sort of water bypass channels may be employed to allow liquid water to pass around the sample cell windows.

The sample cell is heated all over by heater 137, which is part of the infrared humidity sensor unit 139. This heater comes into contact with the sample cell 138 when the sample cell is inserted into the infrared humidity sensor. The purpose of heater 137 is to stop condensation from forming anywhere in the sample cell. The amount of power which is applied to the heater is carefully regulated so that the air which passes through the sample cell is not heated or cooled by the sample cell. It is important that the air enters and leaves the sample cell at the same temperature, because if the temperature is changed by the sensor then the humidity sensor will change the system it is trying to measure.

It may also be necessary to prevent airborne particles and water droplets from landing on the sample cell windows. To prevent this from happening a "tortuous path" baffle may be used, as shown in FIG. 11. This sample cell is of the same type as that shown in FIG. 10, but with the addition of baffles 141, 142. These baffles force the air to move around them and any large water particles tend to drop out onto the surface of these baffles, It is very important to keep the windows of the sample cell clean for the infrared gas analyser to work properly. To assist in this window covers may be provided which am pulled off or removed before the sample cell is fitted into the sensor unit. These will keep the sample cell windows free from accidental fingerprints, dust and scratches which may occur during handling.

Before use the infrared humidity sensor needs to be calibrated with a sample cell full 15 dry air. This is necessary because each sample cell will have different infrared transmission characteristics. To accomplish this with a flowing source of dry air is not always convenient in practice, so it is proposed to supply the sample cell to the user completely sealed with end caps and filled with dry air. This means that the user just has to fit the sample cell into the infrared humidity sensor, perform calibration, and remove the end caps for correct operation of the humidity sensor,

We claim:

1. Apparatus for measuring the humidity of a gas or a mixture of gases flowing in a medical breathing circuit, said apparatus comprising a source of infrared radiation of one or more selected wavelengths including a wavelength strongly absorbed by water, a gas sample cell through which the radiation is passed and through which said gas or gases pass in use, an infrared radiation detector adapted to detect radiation in said one or more selected wavelengths, means defining a radiation path between said source and said detector with said sample cell being positioned intermediately of said source and said detector, signal processing means connected to the output of said detector which convert the intensity of the received infrared radiation on said detector to a signal proportional to the humidity of the gases passing through said sample cell and water-prevention means associated with said sample cell which prevent water entering or forming in the sample cell said sample cell incorporating at least one radiation transparent window and said water prevention means comprising baffles disposed within the cell around the periphery of said at least one window to prevent liquid water from contacting the window surface.

2. Apparatus according to claim 1 wherein a second set of baffles are disposed within said sample cell to provide a labyrinthic path through which gases must pass before traversing the surface of said window to thereby induce any liquid water contained in said gases to deposit on said second set of baffles.

3. An infrared gas analyser comprising a source of infrared radiation of at least two selected wavelengths, the first selected wavelength being strongly absorbed by a selected gas to constitute a measurement wavelength and the second selected wavelength selected so as to be minimally absorbed by said selected gas to constitute a reference wavelength, a gas sample cell through which the radiation is passed and through which said gas or gases pass in use, an infrared radiation detector adapted to detect radiation in said selected wavelengths, means defining a radiation path between said source and said detector with said sample cell being positioned intermediately of said source and said detector, a rotating dual segment filter assembly located in said radiation path prior to said sample cell which alternately allows transmission of radiation of the measurement wavelength and then the reference wavelength, a synchronous demodulator fed with the output of said detector and a synchronizing signal produced by sensing the period each segment of said rotating filter is present in the radiation path which converts the output signal from the infrared radiation detector to a signal proportional to the concentration of the selected gas present in the gases passing through said sample cell, a switched power supply for said source of infrared radiation, and means for switching the output of said power supply between two levels, said switching being in phase with said synchronizing signal, said levels being predetermined to ensure the amplitude of the output signal from the infrared radiation detector remains constant when the concentration of said selected gas in said sample cell is zero.

4. An infrared gas analyser according to claim 3 including means which detect blocking intervals when non filter components of the rotating filter assembly pass through the radiation path and gate means which insert into the signal from the output of the infrared radiation detector a zero signal during said blocking intervals.

5. An infrared gas analyser according to claim 4 including gate means which hold the signal from the output of the infrared radiation detector at the level it was immediately before the blocking intervals during the detected blocking intervals.

6. An infrared gas analyser comprising a first source of infrared radiation of a first selected wavelength, the first selected wavelength being strongly absorbed by a selected gas to constitute a measurement wavelength, a second source on infrared radiation of a second selected wavelength, the second selected wavelength, the second selected wavelength selected so as to be minimally absorbed by said selected gas to constitute a reference wavelength, a gas sample cell through which radiation from both the first and second source is passed and through which said gas or gases pass in use, an infrared radiation detector adapted to detect radiation at said selected wavelengths, means defining a radiation path between said sources and said detector with said sample cell being positioned intermediately of said sources and said detector, a synchronous demodulator fed with the output of said detector and a synchronizing signal which converts the output signal from the infrared detector to a signal proportional to the concentration of the selected gas present in the gases passing through said sample cell, a first switched power supply for said first source of infrared radiation, a second switched power supply for said second source of infrared radiation and means for alternately switching the outputs of said first and second power supplies to energize alternately the respective first and second sources of infrared radiation, said switching being in phase with said synchronizing signal, means for setting the levels of the power supply outputs, said levels being predetermined to ensure the amplitude of the output signal from the infrared radiation detector remains constant when the concentration of said selected gas in said sample cell is zero, radiation combining means in said radiation path prior to said sample cell which combines radiation from said first source of infrared radiation with radiation from said second source of radiation, and said combining means is also a radiation splitting means which derives a further radiation path of combined radiation and including a second infrared radiation detector positioned in said further radiation path, a second synchronous demodulator fed with the output of said second infrared radiation detector and said synchronizing signal which produces a signal representative of the imbalance of radiation intensities generated by the first and second infrared radiation sources respectively, and means responsive to said imbalance signal which controls the outputs of both power supplies to keep the ratio of the radiation intensities from the first and second infrared radiation sources constant.

7. Apparatus for measuring the humidity of a gas or a mixture of gases flowing in a medical breathing circuit, said apparatus comprising a source of infrared radiation of one or more selected wavelengths including a wavelength strongly absorbed by water, a gas sample cell through which the radiation is passed and through which said gas or gases pass in use, an infrared radiation detector adapted to detect radiation in said one or more selected wavelengths, means defining a radiation path between said source and said detector with said sample cell being positioned intermediately of said source and said detector, signal processing means connected to the output of said detector which convert the intensity of the received infrared radiation on said detector to a signal proportional to the humidity of the gases passing through said sample cell and water-prevention means associated with said sample cell which prevent water entering or forming in the sample cell, said water prevention means comprising a microporous envelope provided about said sample cell.

* * * * *